US00PP33226P3

(12) United States Plant Patent
Pierron-Darbonne

(10) Patent No.: US PP33,226 P3
(45) Date of Patent: Jul. 6, 2021

(54) BLACKBERRY PLANT NAMED 'PLABLACK 15157'

(50) Latin Name: ***Rubus* subgenus *Eubatus* sect. *Morifieri* & *Ursini* and hybrids**
Varietal Denomination: Plablack 15157

(71) Applicant: Plantas de Navarra, S.A. Sociedad Unipersonal, Navarra (ES)

(72) Inventor: Alexandre Pierron-Darbonne, Pamplona (ES)

(73) Assignee: Plantas de Navarra, S.A. Sociedad Unipersonal, Navarra (ES)

( * ) Notice: Subject to any disclaimer, the term of this patent is extended or adjusted under 35 U.S.C. 154(b) by 0 days.

(21) Appl. No.: 16/602,038

(22) Filed: Jul. 25, 2019

(65) Prior Publication Data

US 2020/0128714 P1 Apr. 23, 2020

(30) Foreign Application Priority Data

Oct. 23, 2018 (QZ) ..... PBR 2018/2666
Jan. 25, 2019 (MA) ..... 901/19

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./203
CPC ..... A01H 6/7499
See application file for complete search history.

*Primary Examiner* — Anne Marie Grunberg
(74) *Attorney, Agent, or Firm* — Knobbe, Martens, Olson & Bear, LLP

(57) ABSTRACT

A new and distinct variety of blackberry plant 'Plablack 15157' is characterized by a combination of traits which include, but are not limited to, an absent or very weak anthocyanin coloration of dormant cane, many spines density, a pinkish color of petals and abundant production of elliptic to narrow ovate shaped, and medium fruit size.

20 Drawing Sheets

Botanical classification: *Rubus* subgenus *Eubatus* sect. *Morifieri* & *Ursini* and hybrids.

Variety denomination: The new plant has the varietal denomination 'Plablack 15157'.

CROSS-REFERENCE TO RELATED APPLICATIONS

This application claims the benefit of European Community Plant Variety Office Application No. 2018/2666, for a blackberry variety named 'Plablack 1401', filed on Oct. 23, 2018, the entirety of which is incorporated by reference herein. It also claims the benefit of Moroccan Plant Variety Application No. 901/19, filed Jan. 25, 2019.

BACKGROUND

The new variety of blackberry was created in a breeding program by crossing two parents; in particular, by crossing a seed parent of an undistributed blackberry parent designated '14:101R' (unpatented) and a pollen parent of an undistributed blackberry parent designated '13:135R' (unpatented). Female and male are selections from the breeder's program of the Applicant. Both parental varieties are property of the Applicant and have not been commercialized.

The resulting seedling of the new variety was grown and asexually propagated by roots cuttings in Segovia, Spain, 3°59'W., 41°22'N., 2742 feet elevation. Clones of the new variety were further asexually propagated and extensively tested. This propagation and testing has demonstrated that the combination of the traits disclosed herein, which characterize the new variety, are fixed and retained true to type through successive generations of asexual reproduction.

SUMMARY

The present invention relates to a new and distinct blackberry variety. The varietal denomination of the new variety is 'Plablack 15157'. The new variety shows a primocane fruiting habit, produces and maintains a strong vigorous plant with consistent fruit production from beginning October through ending December on primocanes and in the ensuing year from beginning May through the middle June.

Among the characteristics which appear to distinguish the new variety from other varieties are a combination of traits which include an absent or very weak anthocyanin coloration of dormant cane, many spines density, a pinkish color of petals and abundant production of elliptic to narrow ovate shaped, and medium fruit size.

COMPARISON TO THE PARENTS

The new variety is distinguished therefrom its parents by the following characteristics possessed by 'Plablack 15157' which are different than, or not possessed, by the seed parent designated '14:101R' (unpatented) and the pollen parent designated '13:135R' (unpatented).

The seed parent '14:101R' (unpatented) shows a higher intensity of green color on the upper side of the leaf than the new variety 'Plablack 15157'.

The color of the petal in the flower of the seed parent '14:101R' (unpatented) is white with violet tinge, whereas color of the petal in the flower of the new variety 'Plablack 15157' is pinkish (RHS red:purple group near 68 B to 68 A, and whitish pigmentation (RHS white group near 155 A) at the base).

The seed parent '14:101R' (unpatented) shows a higher glossiness on the upper side of the leaf than the new variety 'Plablack 15157'.

The color of petal in the flower of the pollen parent '13:135R' (unpatented) is white, whereas color of the petal in the flower of the new variety 'Plablack 15157' is pinkish (RHS red:purple group near 68 B to 68 A, and whitish pigmentation (RHS white group near 155 A) at the base).

The pollen parent '13:135R' (unpatented) shows a broader petal than the new variety 'Plablack 15157'.

COMPARISON TO CLOSEST VARIETY

The new variety is closest to the variety 'Reuben' (U.S. Plant Pat. No. 23,497), but is distinguished therefrom by the following characteristics possessed by 'Plablack 15157' which are different than, or not possessed by, 'Reuben' (U.S. Plant Pat. No. 23,497).

'Reuben' (U.S. Plant Pat. No. 23,497) shows smaller spines density in the dormant cane than 'Plablack 15157'.

The spines of 'Reuben' (U.S. Plant Pat. No. 23,497) are shorter than 'Plablack 15157'.

The cross section of the dormant cane of 'Reuben' (U.S. Plant Pat. No. 23,497) is rounded to angular shaped, whereas the dormant cane of 'Plablack 15157' is angular shaped.

The terminal leaflet of 'Plablack 15157' is longer and broader than the terminal leaflet of 'Reuben' (U.S. Plant Pat. No. 23,497).

The upper side of the leaf of 'Reuben' (U.S. Plant Pat. No. 23,497) shows a green color (RHS green color near 139 B to 139 A), whereas the upper side of the leaf of 'Plablack 15157' shows a green color (RHS green group near 141 C to 141B).

The glossiness of the upper side of the leaf of 'Plablack 15157' is stronger than the glossiness shown in the upper side of the leaf of 'Reuben' (U.S. Plant Pat. No. 23,497).

The base of terminal leaflet of 'Reuben' (U.S. Plant Pat. No. 23,497) shows an acute shape, whereas the base of terminal leaflet of 'Plablack 15157' shows a rounded shape.

'Reuben' (U.S. Plant Pat. No. 23,497) shows a white petal color (RHS white group color near 155 D to 155 C), whereas 'Plablack 15157' shows a red purple color (RHS red:purple group near 68 B to 68 A) and whitish pigmentation (RHS white group near 155 A) at the base.

'Reuben' (U.S. Plant Pat. No. 23,497) maintains petals stuck to the fruits during the development and maturing stages of the fruits. 'Plablack 1401' does not present petals stuck to the fruits.

'Reuben' (U.S. Plant Pat. No. 23,497) shows a medium ovate shaped fruit and a medium fruit size, whereas 'Plablack 15157' shows an elliptic to narrow ovate shaped fruit and a longer and narrower fruit size than 'Reuben' (U.S. Plant Pat. No. 23,497).

Time of beginning of flowering on current year's cane and time of beginning of fruit ripening on previous year's cane of 'Reuben' (U.S. Plant Pat. No. 23,497) is early, whereas in 'Plablack 15157' it is very early.

Differences of spines density and size of spines in canes of 'Plablack 15157' (designated 15.21R.06) and 'Reuben' (U.S. Plant Pat. No. 23,497) are shown in FIG. 16.

Difference between cross section of dormant cane of 'Reuben' (U.S. Plant Pat. No. 23,497) and 'Plablack 15157' (designated 15.21R.06) are shown in FIG. 17.

Differences in ratio length/width of the terminal leaflet and shape of base of the terminal leaflet of 'Plablack 15157' (designated 15.21R.06) and 'Reuben' (U.S. Plant Pat. No. 23,497) are shown in FIG. 18.

Differences in color and glossiness of the leaf of 'Plablack 15157' (designated 15.21R.06) and 'Reuben' (U.S. Plant Pat. No. 23,497) are shown in FIG. 18.

Differences in petal color of 'Plablack 15157' (designated 15.21R.06) and 'Reuben' (U.S. Plant Pat. No. 23,497) are shown in FIG. 19.

Difference in maintenance of petals stuck to the fruits during the development and maturing of the fruits between 'Plablack 15157' (designated 15.21R.06) and 'Reuben' (U.S. Plant Pat. No. 23,497) are shown by comparing FIG. 1 and FIG. 2 (designated 15.21R.06) with FIG. 15 ('Reuben').

Differences in fruit shape and fruit size of 'Plablack 15157' (designated 15.21R.06) and 'Reuben' (U.S. Plant Pat. No. 23,497) are shown by comparing FIG. 13, FIG. 14 (designated 15.21R.06) with FIG. 20 ('Reuben').

BRIEF DESCRIPTION OF THE ILUSTRATIONS

The accompanying photographs show typical specimens of the new variety, designated 15.21R.06 in the illustrations, including fruit, foliage and flower, in color as nearly true as it is reasonably possible to make in color illustrations of this character.

The plants depicted in the drawings were planted June 1 in Cartaya (Huelva), Spain, about 7°W, 37°N, 45 feet elevation.

Drawings were taken in December (about December 10 and December 20): minimum temperate about 5° to 6° Centigrade, maximum temperate about 16 to 20° Centigrade and May (about May 15 and May 25): minimum temperate about 13° to 15° Centigrade, maximum temperate about 26 to 29° Centigrade.

FIG. 1 and FIG. 2 shows several plants of the new variety (designated 15.21R.06) which exhibit an upright habit.

FIG. 3 and FIG. 4 show the upperside and the underside, respectively, of a complete leaf of the new variety (designated 15.21R.06). In it, we can see that the leaf color of the upper side of the new variety (designated 15.21R.06) is a green color (RHS green group near 141 C to 141 B) and the leaf color of the underside of the new variety (designated 15.21R.06) is RHS green group color (near 143 B to 143 A) and the petiole with very few spines.

FIG. 5 and FIG. 6 show the upperside and the underside, respectively, of the terminal leaflet of the new variety (designated 15.21R.06). In it, we can see that the leaf color of upper side of the new variety (designated 15.21.06) is a green color (RHS Green group near 141 C to 141 B) and the leaf color of underside of the new variety (designated 15.21R.06) is RHS Green group color (near 143 B to 143 A) and the length of the terminal leaflet in the new variety (designated 15.21R.06) is long.

FIG. 7 and FIG. 8 show young shoots and the dormant canes of the new variety (designated 15.21R.06). The young shoots show a green color (RHS Green group near 143 C to 143 B), with a very spread anthocyanin coloration during rapid growth (RHS Greyed-Orange group near 175 D to 176 D), high spines density and typical green color at the base of the spines (RHS Green group color near 142 B to 142 A) and typical green color at the tip of the spines (RHS Green group color near 142 C to 142 B). The dormant canes show a green color (RHS Green group near 143 C to 143 B), with high spines density, typical yellow green color at the base of the spines (RHS Green group color near 145 D to 145 C) and typical greyed orange color at the tip of the spines (RHS Greyed-Orange group color near 176 C to 176 B).

FIG. 9 shows typical flowers of the new variety (designated 15.21R.06).

FIG. 10 shows typical petals of the new variety (designated 15.21R.06) with long flat elliptic shape and red purple color (RHS Red-Purple group near 68 B to 68 A) and whitish pigmentation (RHS White group near 155 A) at the base.

Figure 1:
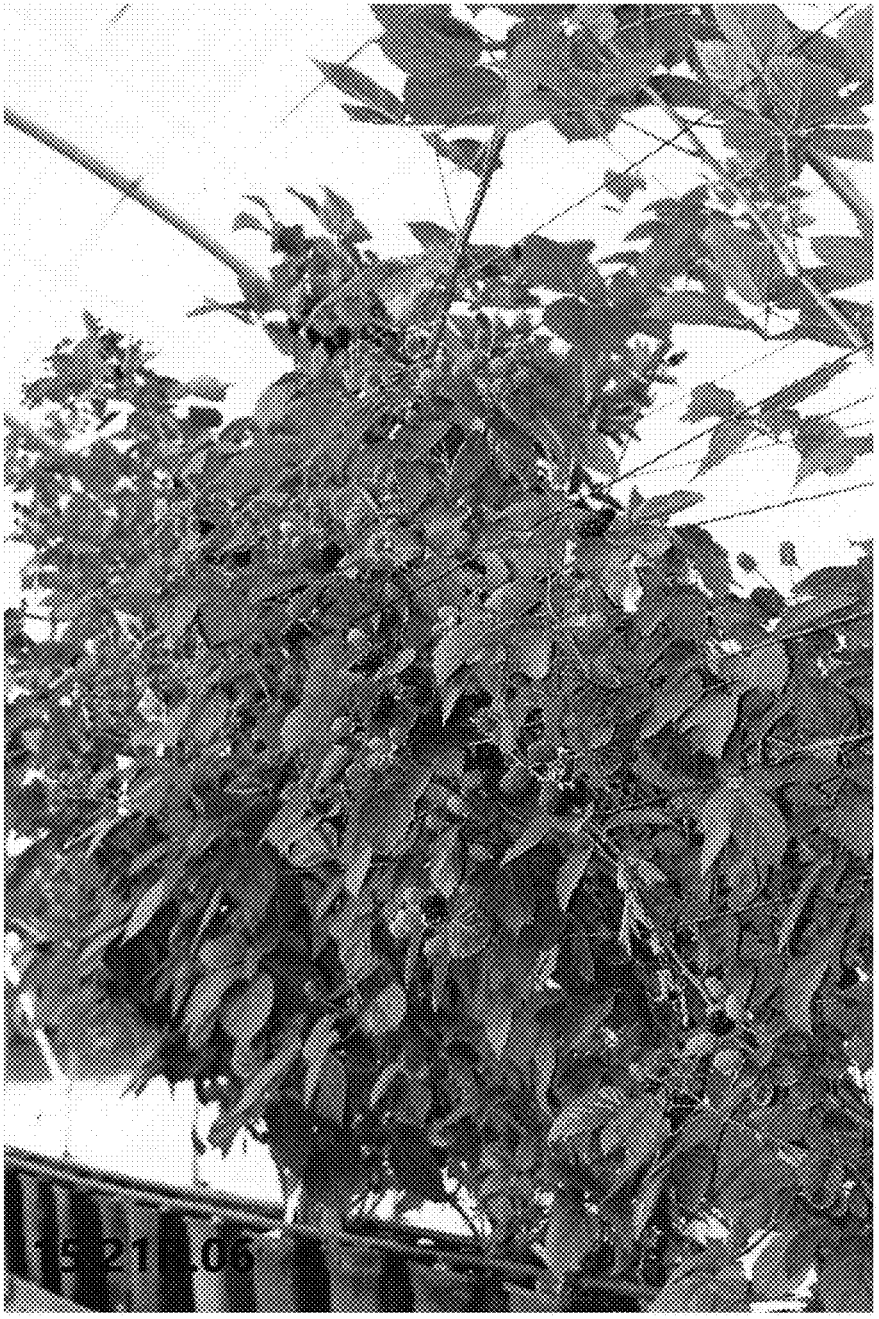
Figure 2:
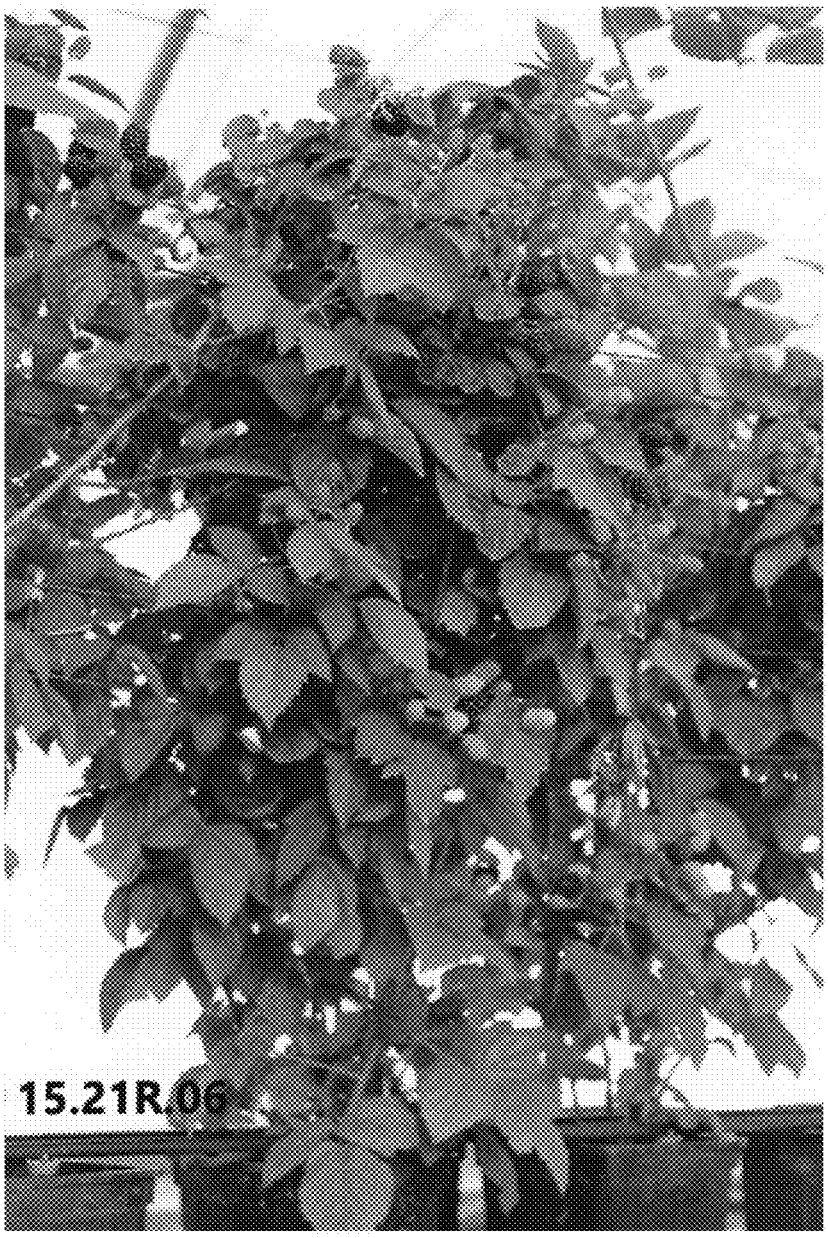
Figure 3:
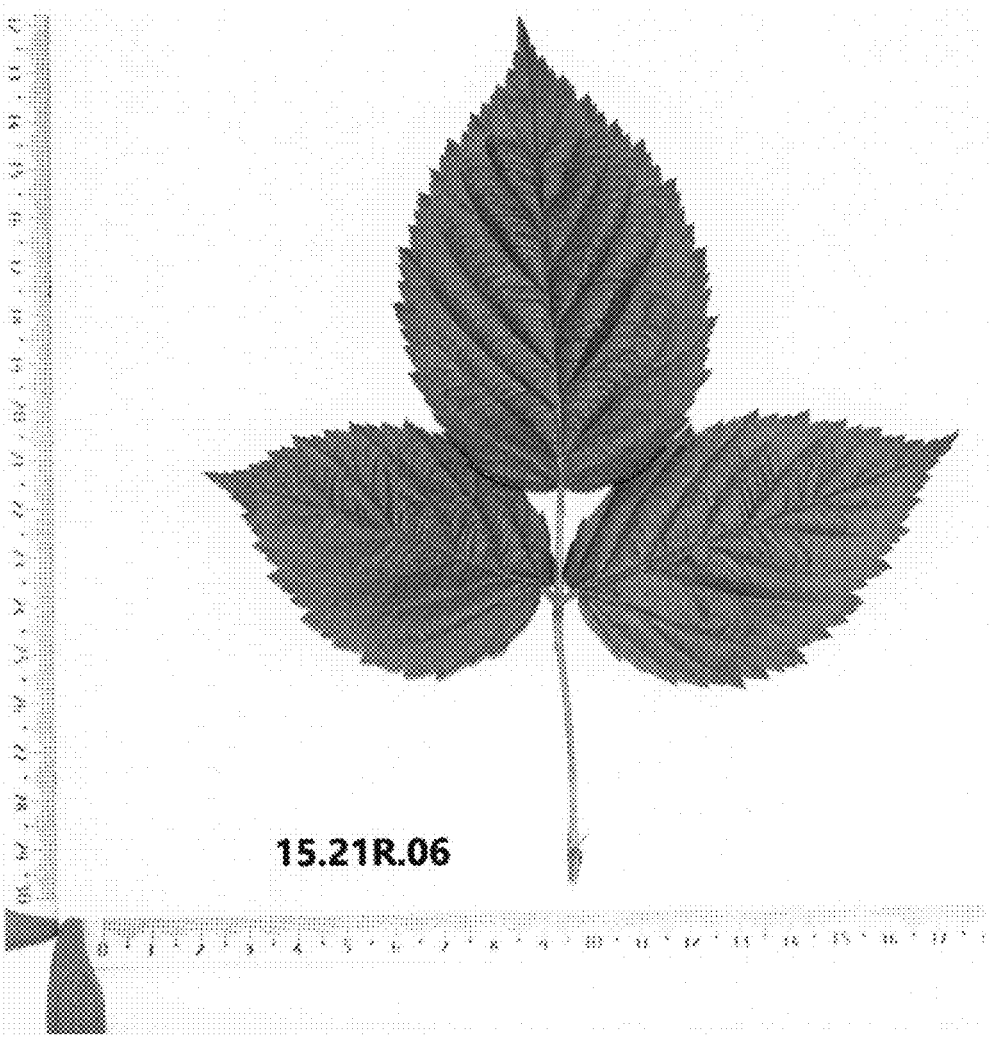
Figure 4:
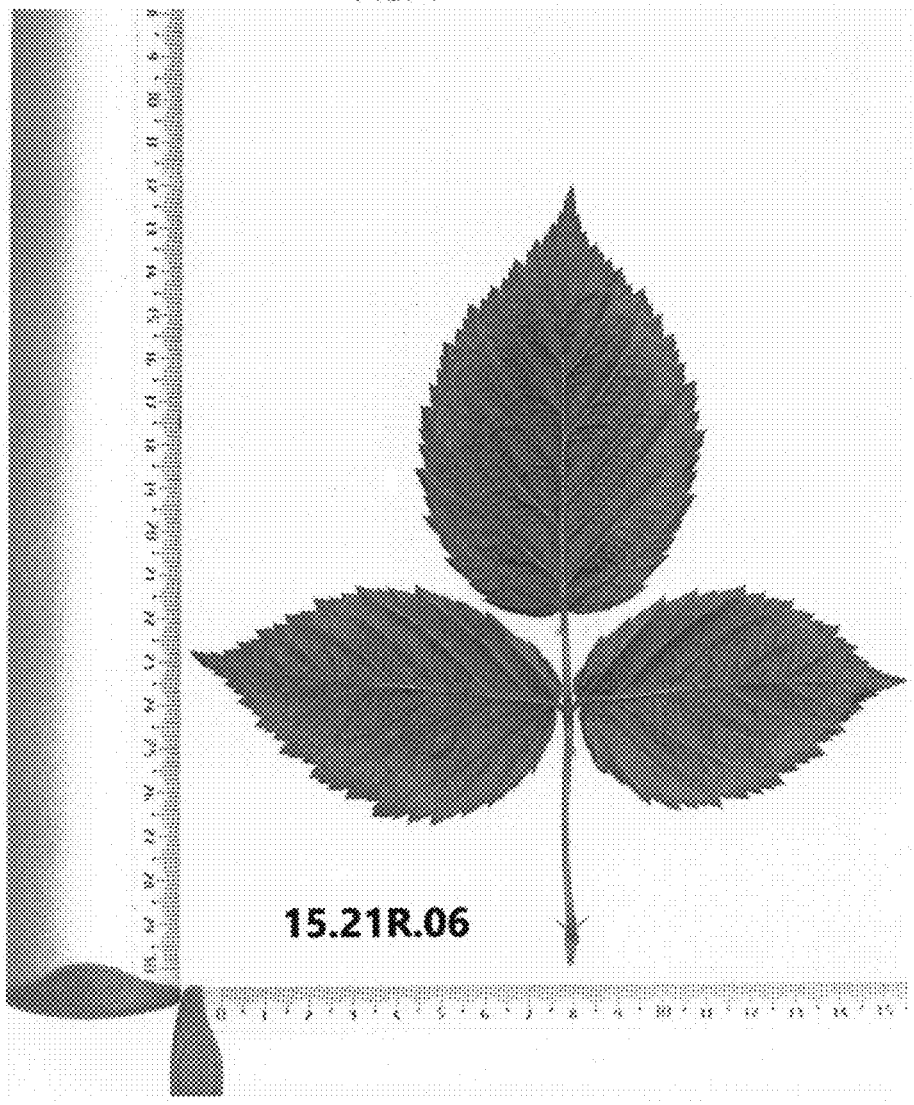
Figure 5:
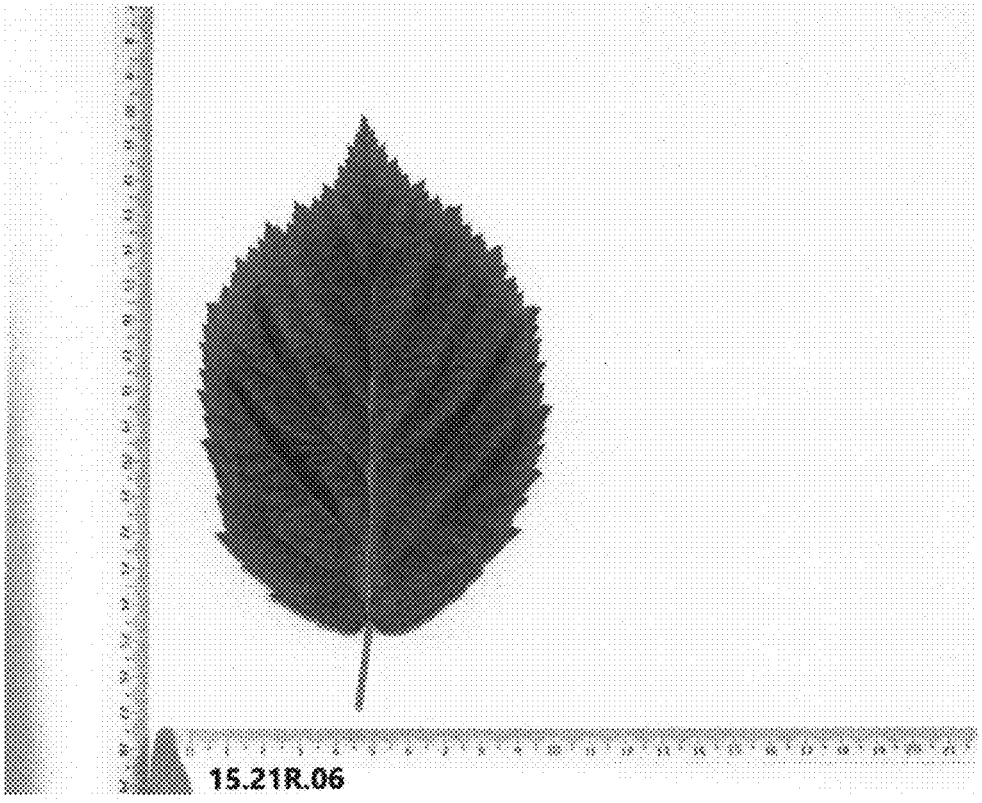
Figure 6:
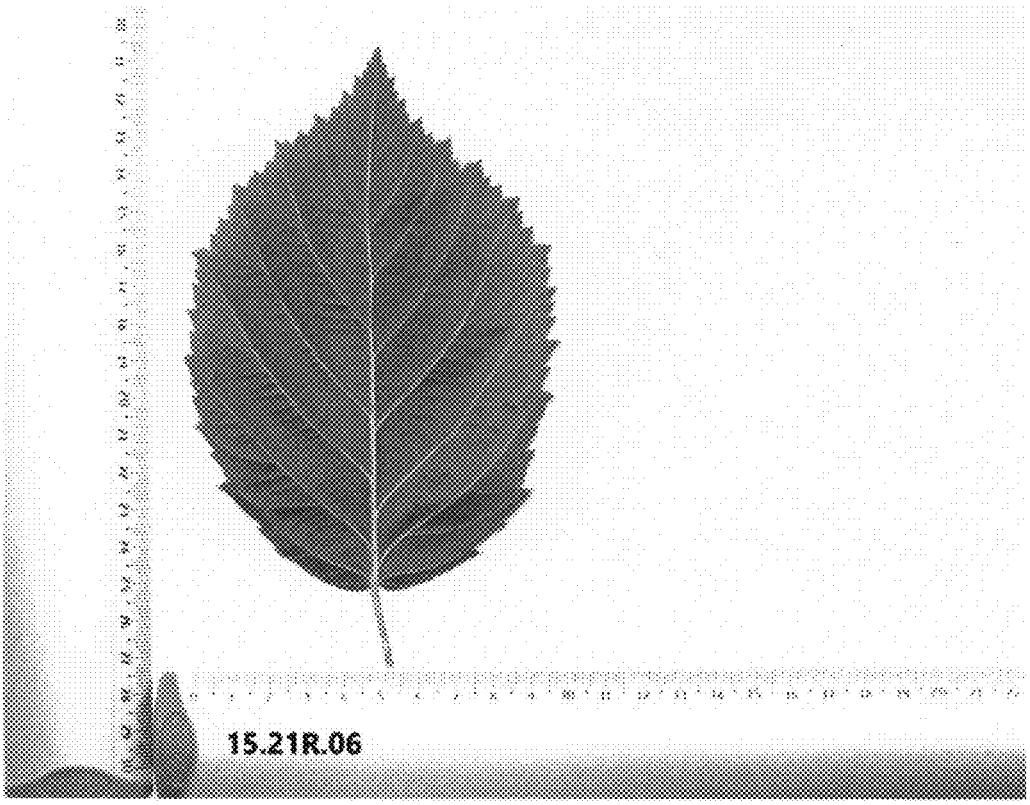
Figure 7:
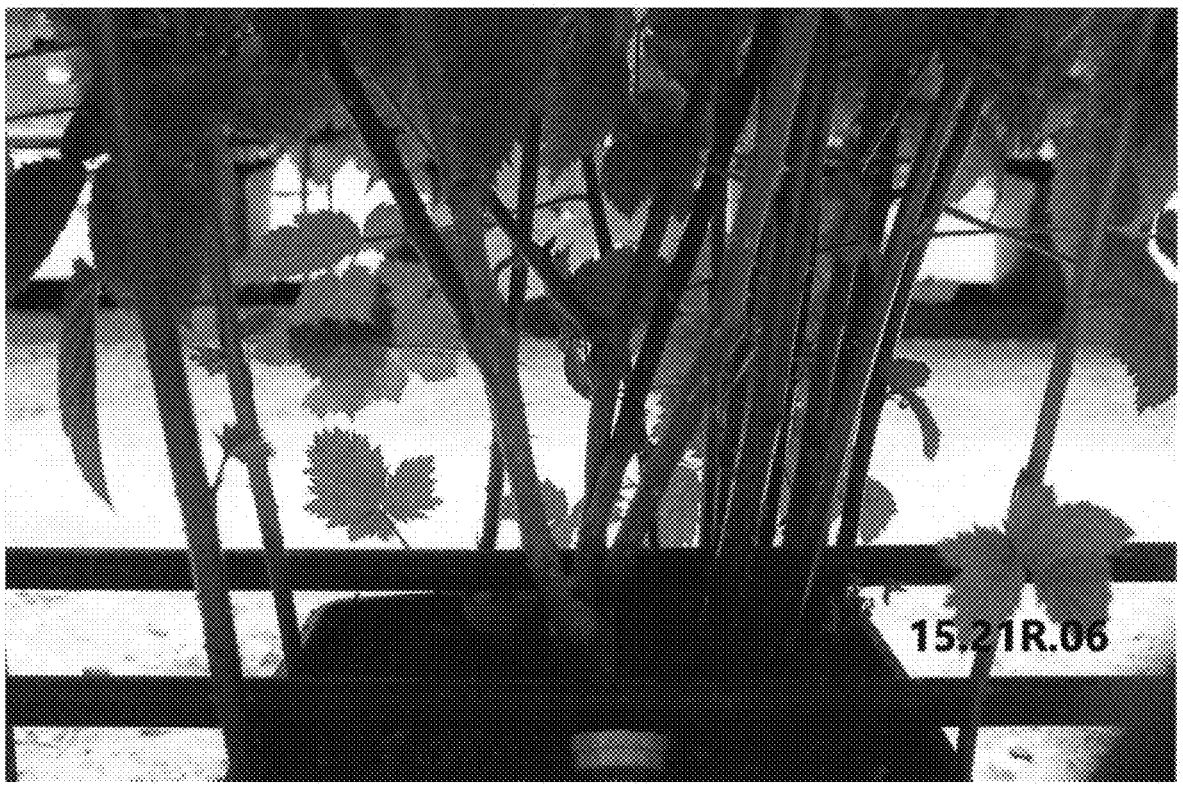
Figure 8:
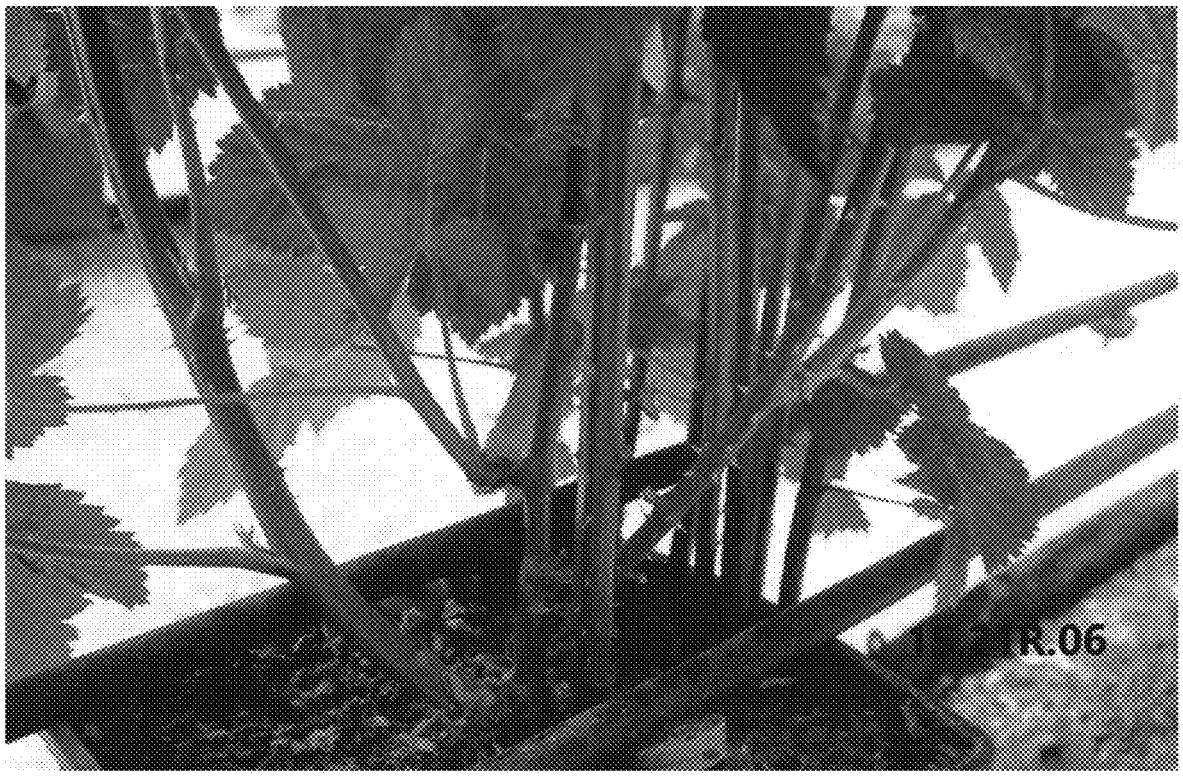
Figure 9:
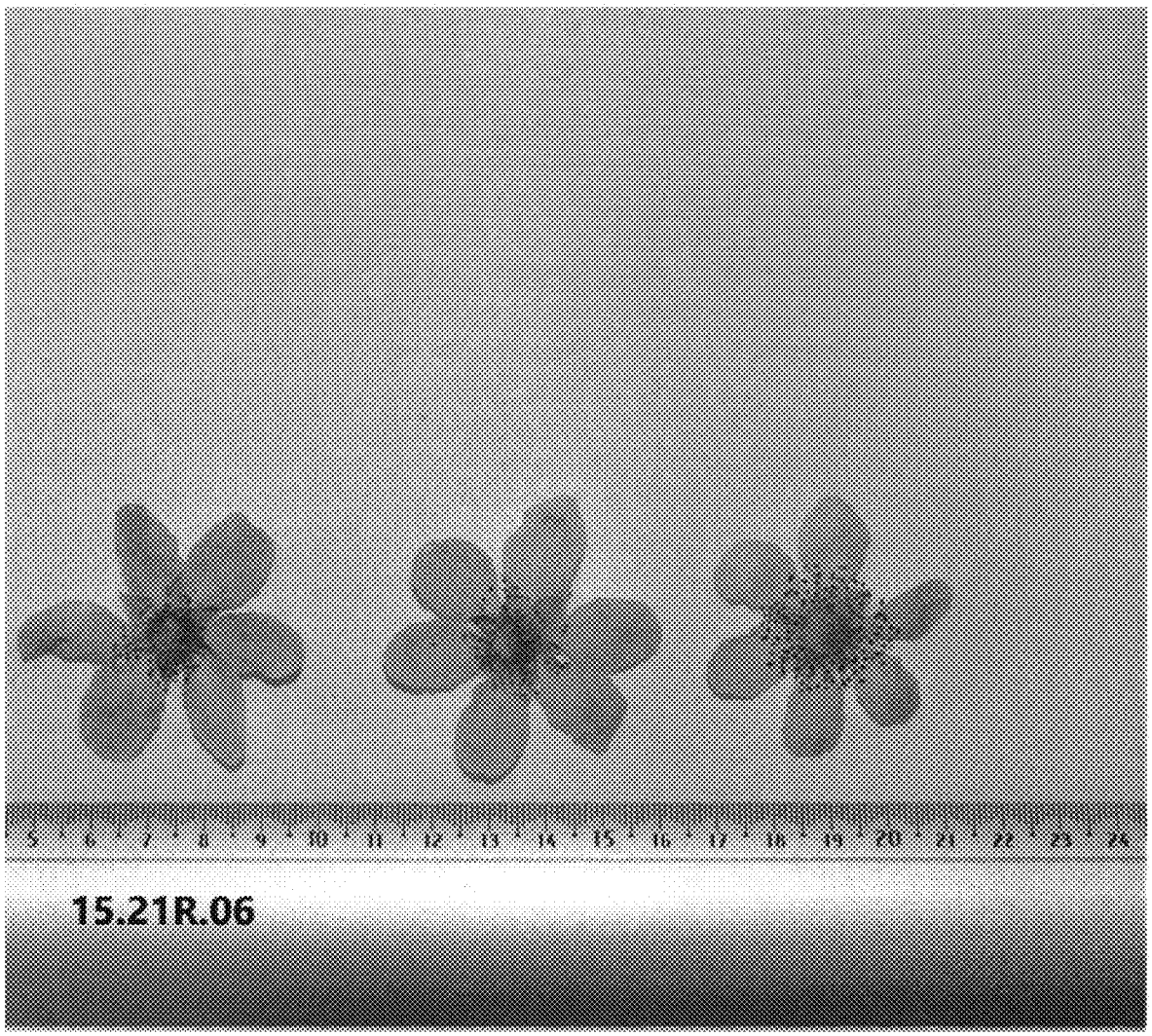
Figure 10:
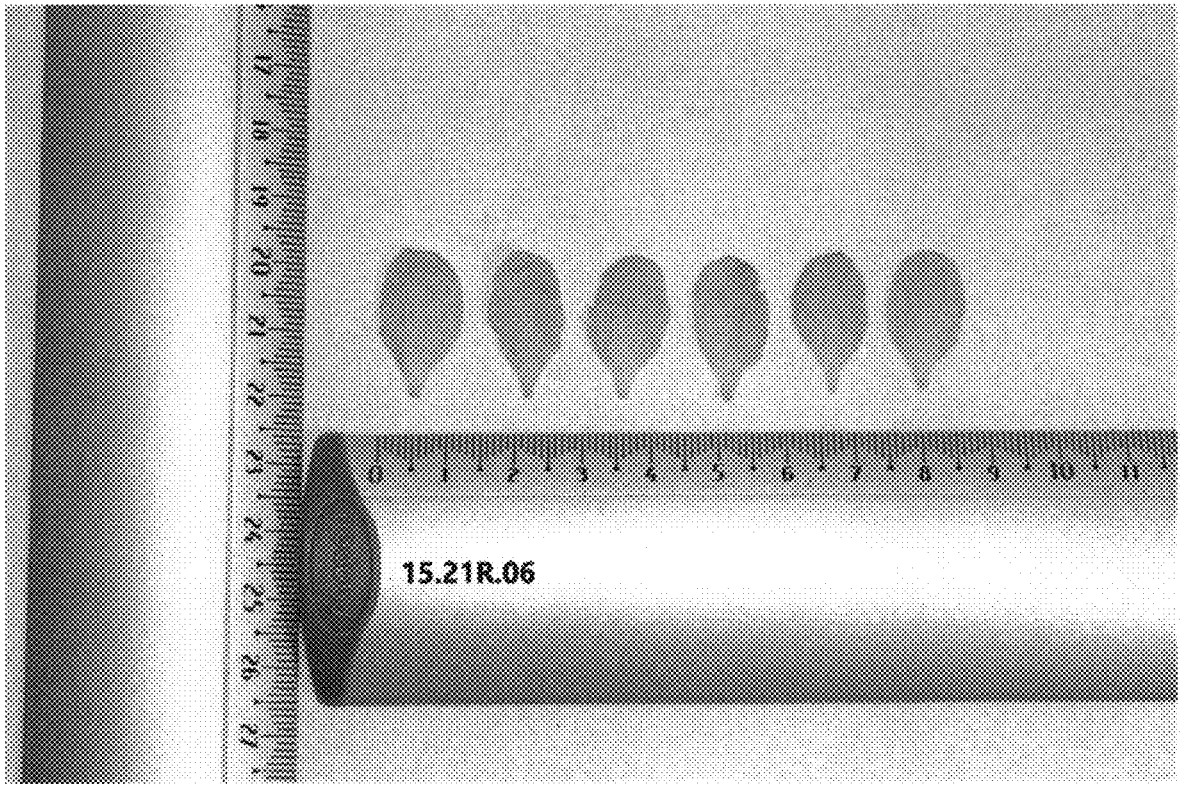
Figure 11:
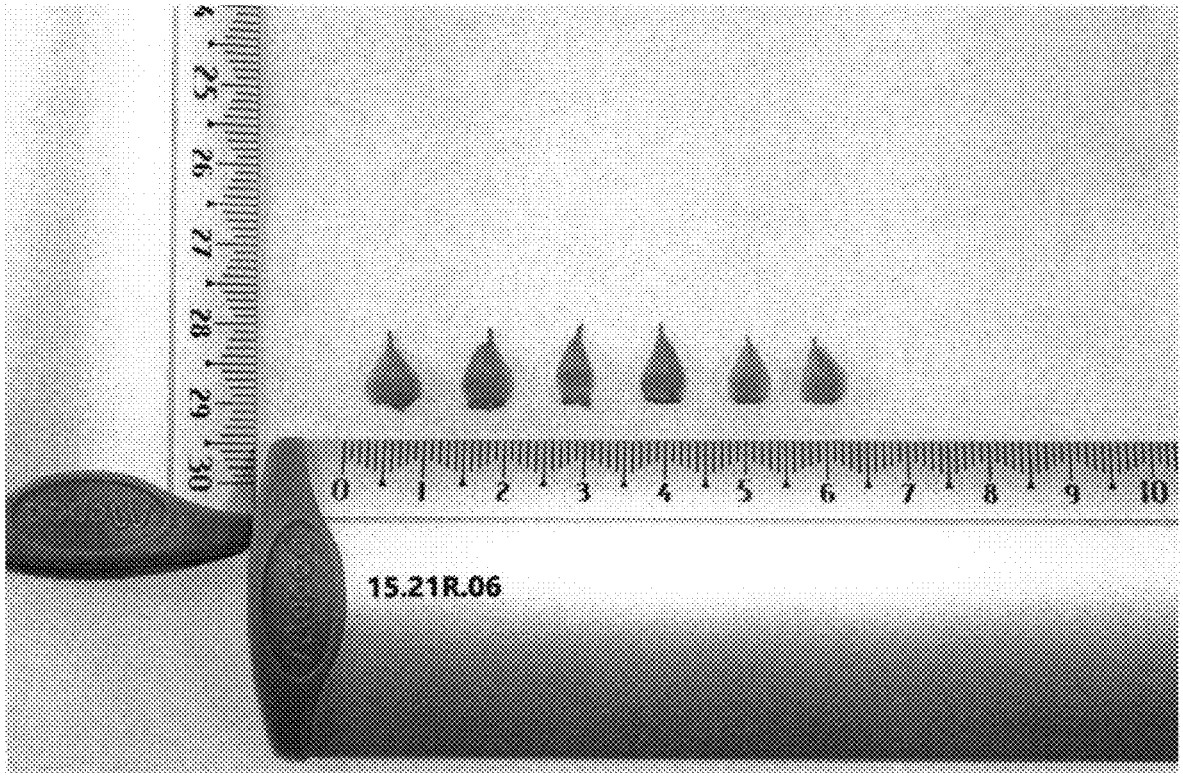
FIG. 11 shows typical sepals of the new variety (designated 15.21R.06) with triangular shape, acuminated apex and yellow green color (RHS Yellow-Green group near 143 C to 143 A).
Figure 12:
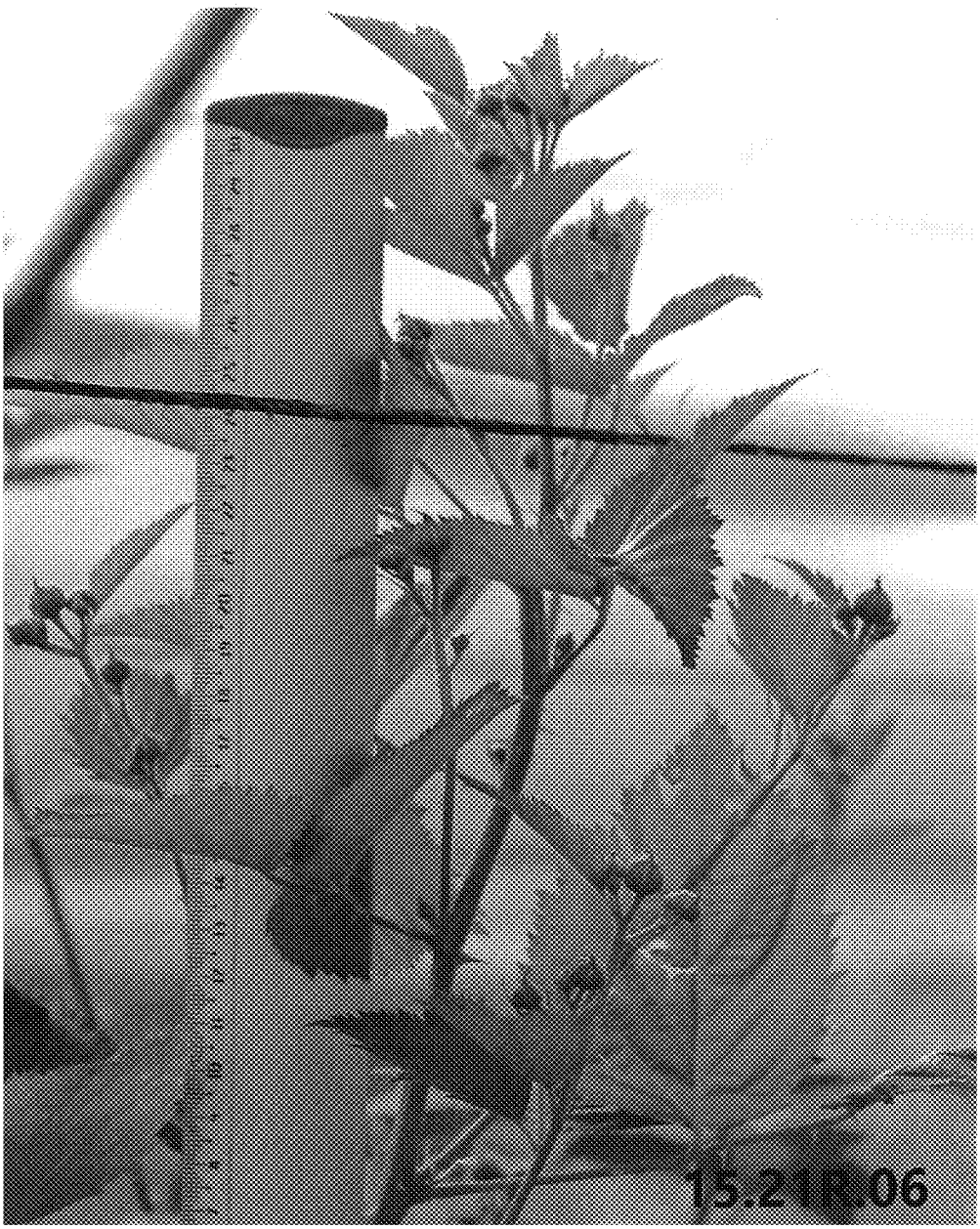
FIG. 12 shows typical flower bud of the new variety (designated 15.21R.06) with rounded shape and green color (RHS Green group near 139 C to 139 B).
Figure 13:
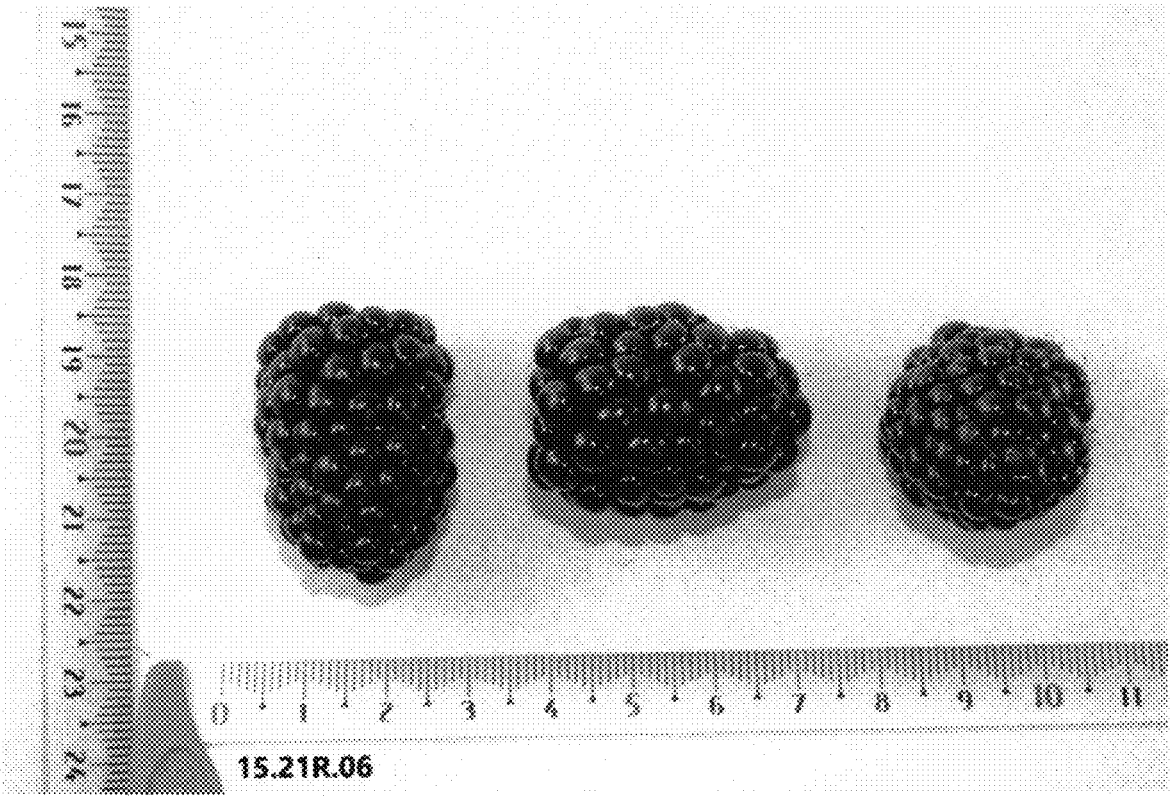
FIG. 13 and FIG. 14 show typical fruits of the new variety (designated 15.21R.06) with elliptic to narrow ovate shape and black color (RHS Black group near 202 A).
Figure 14:
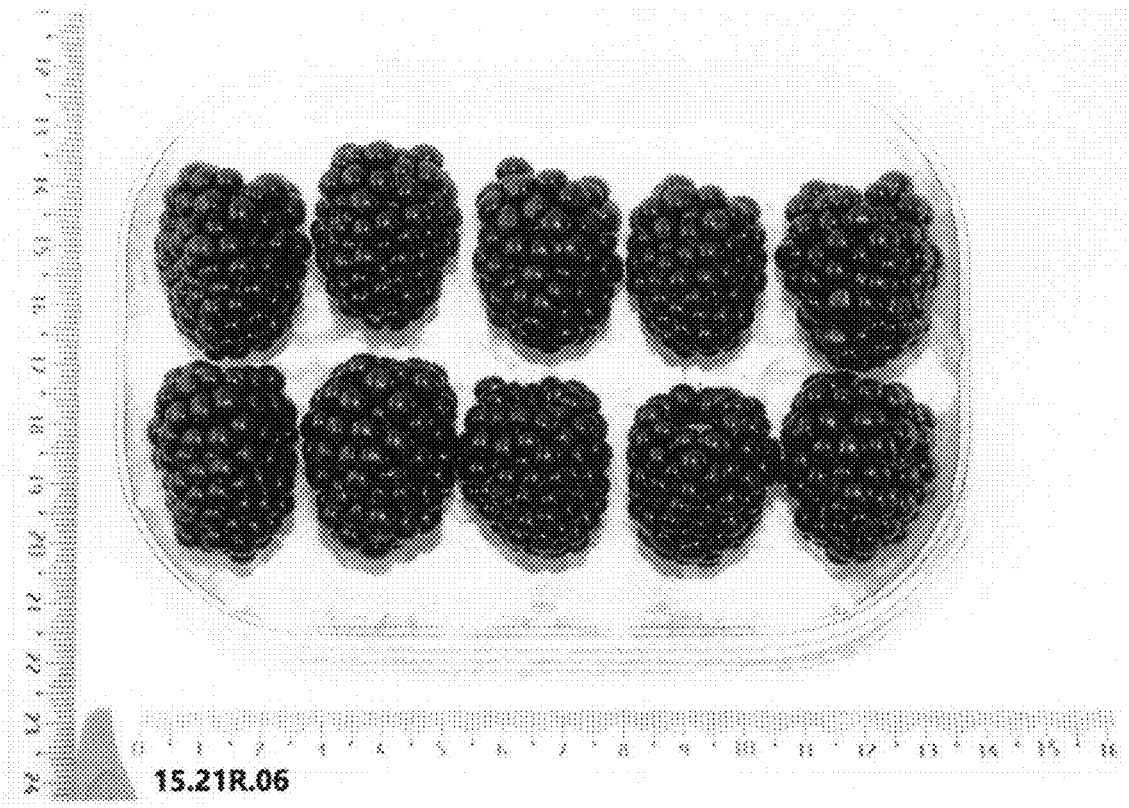
Figure 15:
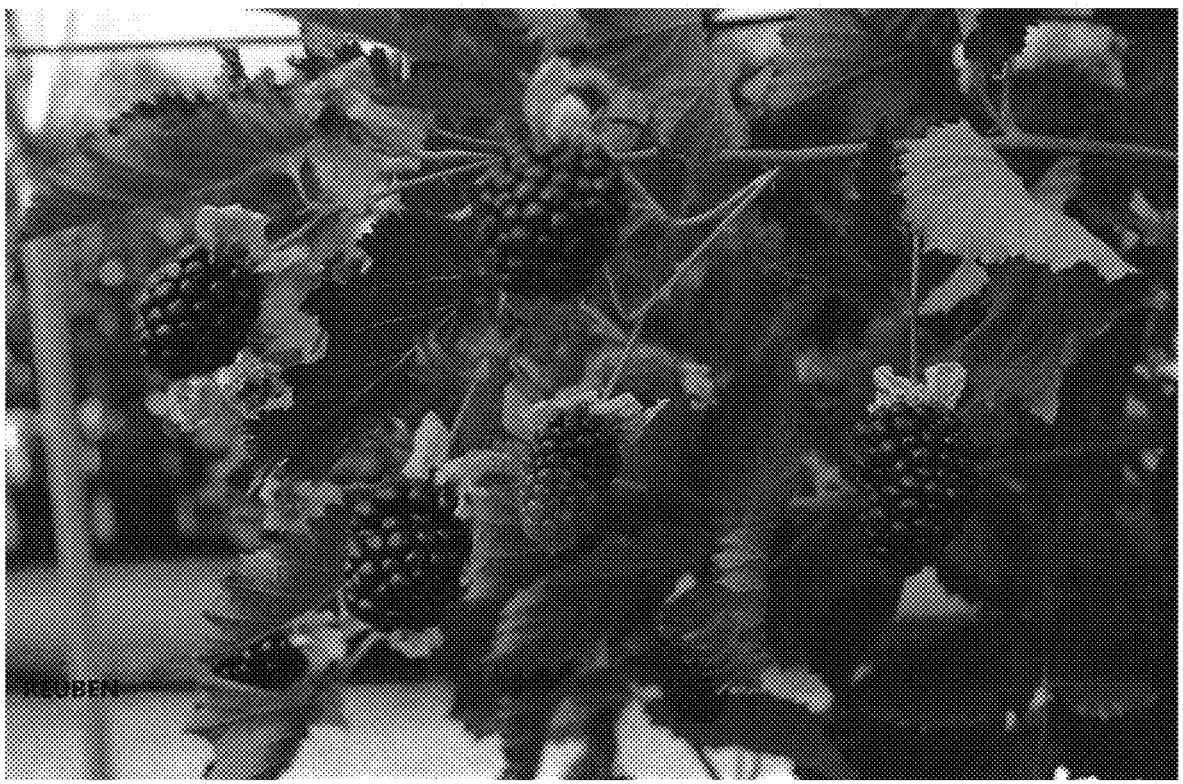

FIG. 15 shows several plants of 'Reuben' (U.S. Plant Pat. No. 23,497), which maintain petals stuck to the fruits during the development and maturing of the fruits.

Figure 16:
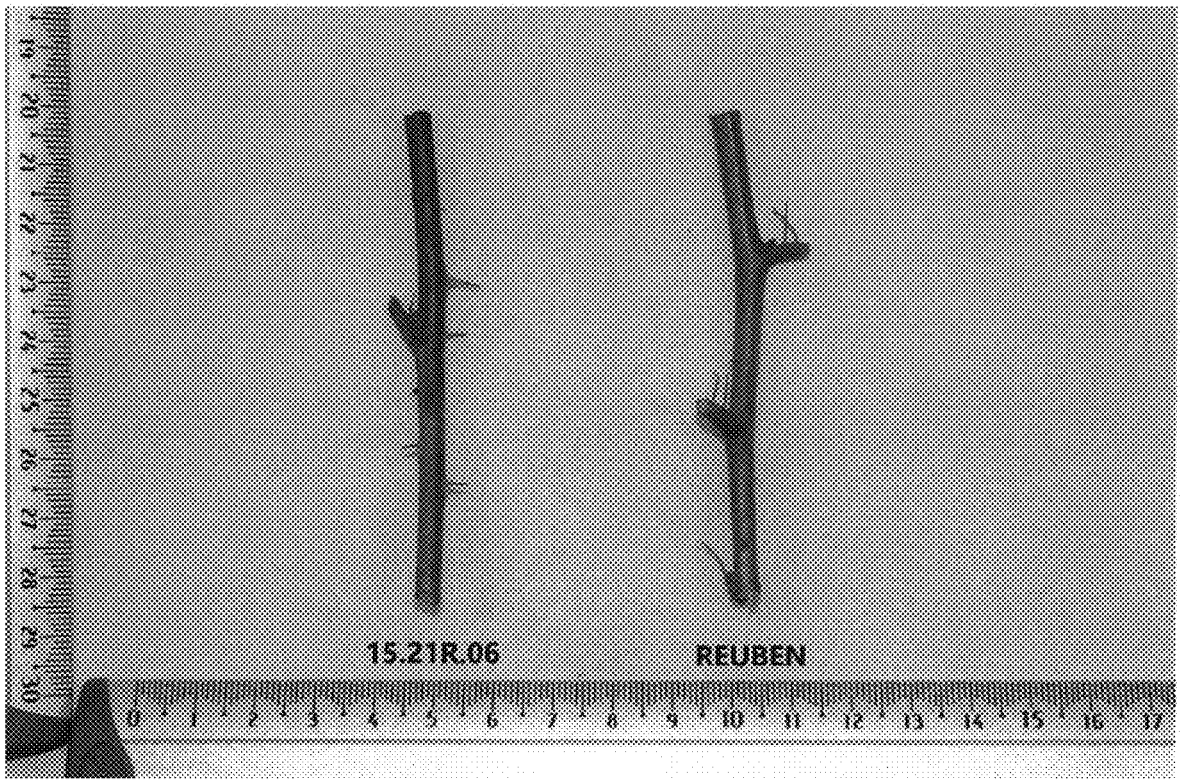

FIG. 16 shows the small spines density and the small size of spines in the canes of 'Reuben' (U.S. Plant Pat. No. 23,497) in comparison with a higher density and size of spines in the canes of the new variety (designated 15.21R.06).

Figure 17:
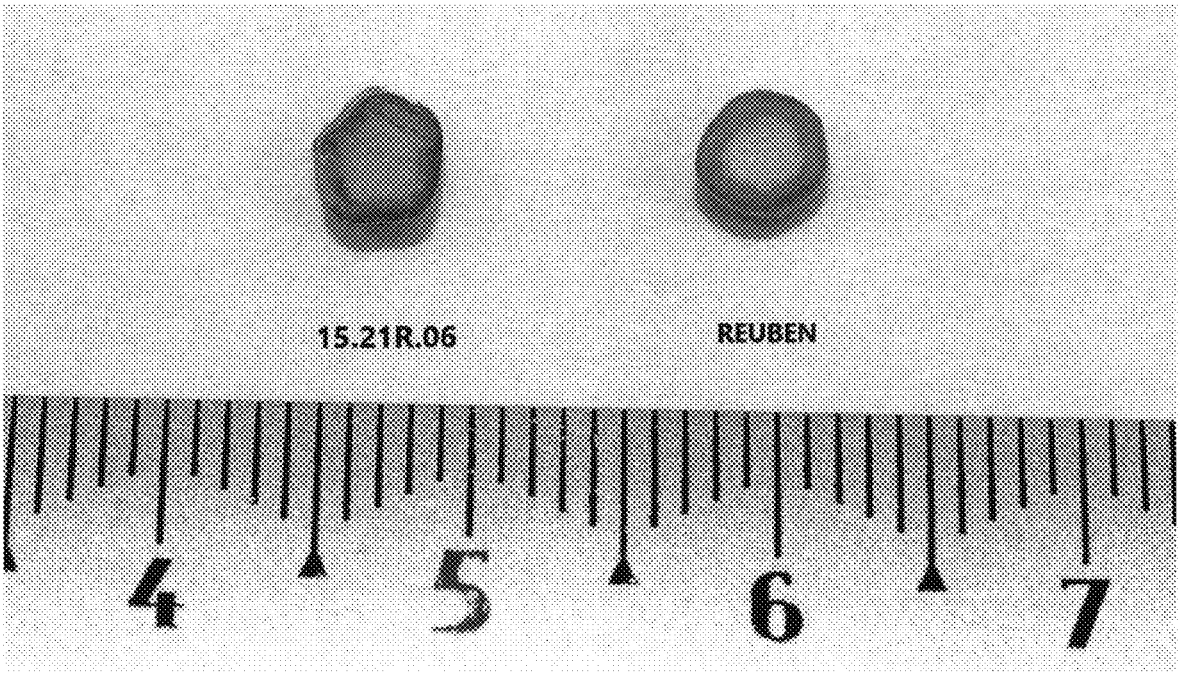

FIG. 17 shows a cross section of the dormant cane of 'Reuben' (U.S. Plant Pat. No. 23,497) with rounded to angular shape in comparison with the cross section of the dormant cane of the new variety (designated 15.21R.06) with angular shape.

Figure 18:
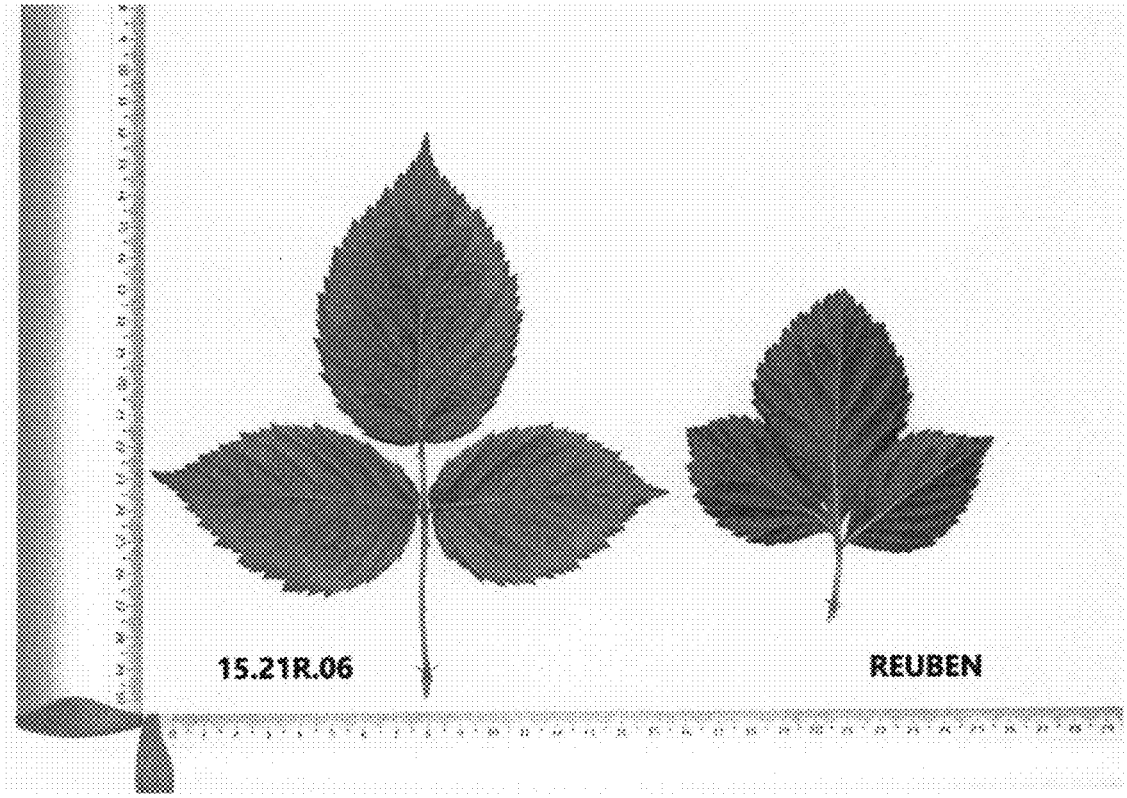

FIG. 18 shows a complete leaf of 'Reuben' (U.S. Plant Pat. No. 23,497) with an upper side green color (RHS Green color near 139 B to 139 A), without spines in the petiole, terminal leaflet moderately longer than broad and an acute shape of the base in comparison with a complete leaf of the new variety (designated 15.21R.06) with an upper side green color (RHS Green group near 141 C to 141B), very few spines in the petiole, terminal leaflet much longer than broad and a rounded shape of base.

Figure 19:
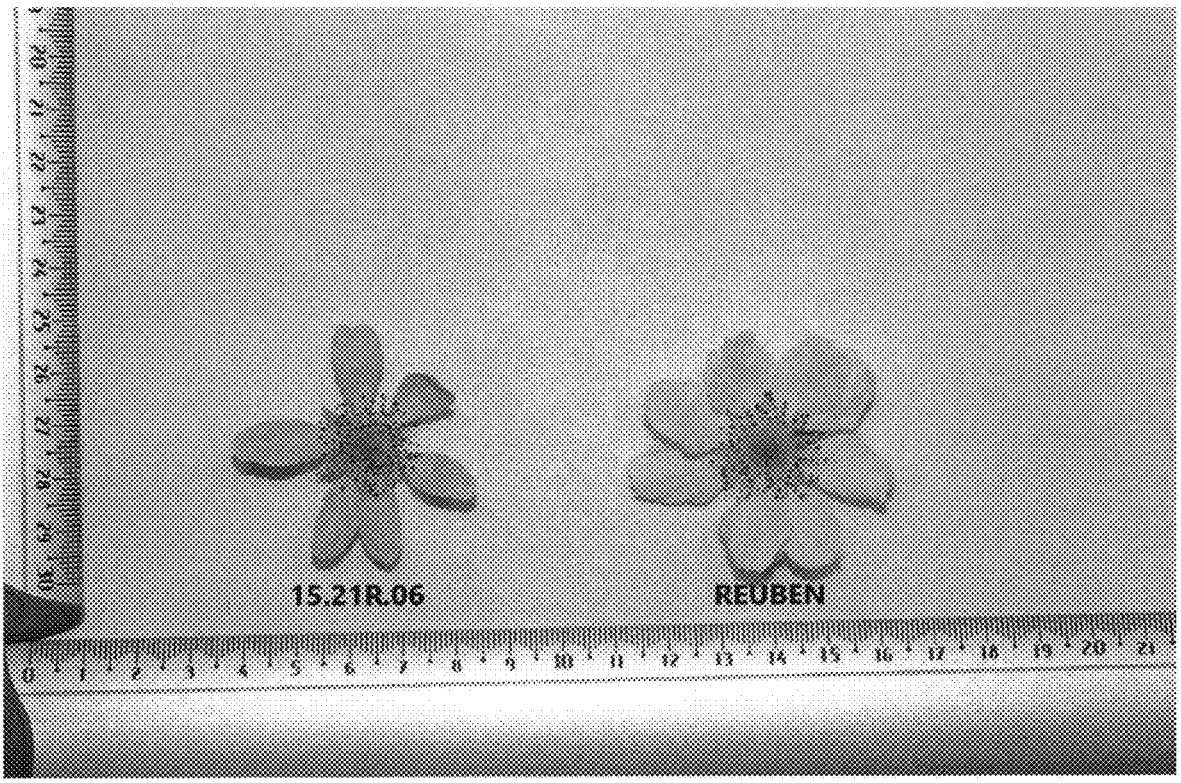

FIG. 19 shows typical flower of 'Reuben' (U.S. Plant Pat. No. 23,497) with a white petal color (RHS White group color near 155 D to 155 C) in comparison with the typical flower of the new variety (designated 15.21R.06) with a red purple petal color (RHS Red-Purple group near 68 B to 68 A) and whitish pigmentation (RHS White group near 155 A) at the base.

Figure 20:
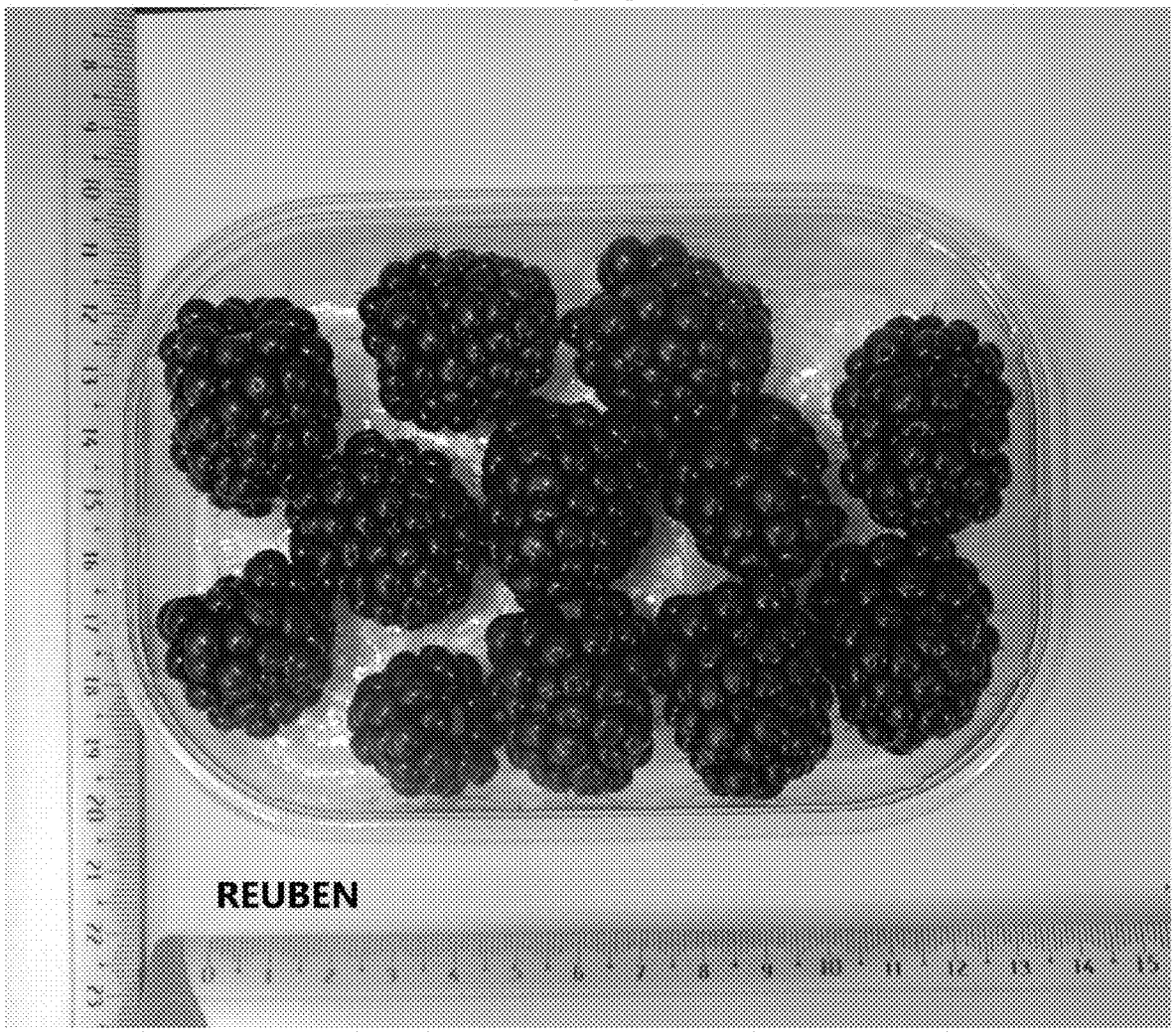

FIG. 20 shows typical fruits with medium ovate shaped fruit and a medium fruit size of 'Reuben' (U.S. Plant Pat. No. 23,497).

DESCRIPTION OF THE NEW VARIETY

The following description is in accordance with UPOV terminology and the color terminology herein is in accordance with The Royal Horticultural Society Colour Chart (R.H.S.C.C.), 3rd edition published in 1995.

The color descriptions and other phenotypical descriptions may deviate from the stated values and descriptions depending upon variation in environmental, seasonal, climatic and cultural conditions.

Throughout this specification, color names beginning with a small letter signify that the name of that color, as used in common speech is aptly descriptive. Color names beginning with capital letter designate values based upon The R.H.S. Colour Chart published by The Royal Horticultural society, London, England, 1995.

The following detailed description of the new variety is based upon observations taken of plants and fruits grown "underglass", i.e. undertunnel, in the farm of La Mogalla in Cartaya (Huelva), Spain, 7°W., 37°N., 45 feet elevation.

PROPAGATION

The new variety is principally propagated by way of root cuttings. Although propagation by root cuttings is presently preferred, other know methods of propagating raspberry plants may be used.

Blackberries root and develop well after transplanting.

GENERAL

'Plablack 15157' is propagated by root cuttings. It is a primocane variety with fruit production from beginning October through ending December on primocanes and in the ensuing year from beginning May through the middle of June. It is a self:fertile variety. It produces large quantity of pollen throughout the seasons and pollination is good.

Production: Plants described are from high elevation nursery in Segovia, Spain, 3°59'W., 41°22'N., 2742 feet elevation. Trials pursued in Cartaya (Huelva), Spain.

Date of planting (two years): 2nd June and 1st June.

Number of repetitions (every year): 3

Plants per repetition (every year): 100

Table 1 shows the accumulated production of 1st Quality Fruit (g/plant).

TABLE 1

| Variety | Beginning in October and ending in December | Beginning in May and middle June | Total |
|---|---|---|---|
| 'Plablack 15157' | 3391.90 | 1557.90 | 4949.80 |
| 'Reuben' (U.S. Plant Pat. No. 23,497) | 563.50 | 1107.30 | 1670.80 |
| 'Prim ARK-45' | 42.50 | 1136.10 | 1178.60 |

Table 2 shows the accumulated total yield: 1st and 2nd Quality Fruit (g/plant).

TABLE 2

| Variety | 1st + 2nd quality beginning in October and ending in December | 1st + 2nd quality beginning in May and middle June | Total |
|---|---|---|---|
| 'Plablack 15157' | 3425.20 | 1574.60 | 4999.80 |
| 'Reuben' (U.S. Plant Pat. No. 23,497) | 1009.70 | 1211.60 | 2221.30 |
| 'Prim ARK-45' | 68.00 | 1175.10 | 1243.10 |

Table 3 shows the production beginning October and ending in December of First Quality Fruit (1st quality) and Second Quality Fruit (2nd quality) in g/plant.

TABLE 3

| Variety | 1st Quality | 2nd Quality | TOTAL (1st Quality + 2nd Quality) | % 2nd Quality |
|---|---|---|---|---|
| 'Plablack 15157' | 3391.90 | 33.30 | 3425.50 | 0.97 |
| 'Reuben' (U.S. Plant Pat. No. 23,497) | 563.50 | 446.20 | 1009.70 | 44.19 |
| 'Prim ARK-45' | 42.00 | 26.00 | 68.00 | 38.23 |

% 2nd Quality = (2nd Quality/TOTAL) × 100

Table 4 shows the production beginning May and ending at the middle June of First Quality Fruit (1st quality) and Second Quality Fruit (2nd quality) in g/plant.

TABLE 4

| Variety | 1st Quality | 2nd Quality | TOTAL (1st Quality + 2nd Quality) | % 2nd Quality |
|---|---|---|---|---|
| 'Plablack 15157' | 1557.90 | 46.70 | 1574.60 | 1.06 |
| 'Reuben' (U.S. Plant Pat. No. 23,497) | 1107.30 | 104.30 | 1211.60 | 8.60 |
| 'Prim ARK-45' | 1136.10 | 39.00 | 1175.10 | 3.31 |

% 2nd Quality = (2nd Quality/TOTAL) × 100

Table 5 shows Weight (g/Fruit) in two production periods: beginning October to end December/beginning May to middle June.

TABLE 5

| Variety | Beginning October to end December | Beginning May to middle June |
|---|---|---|
| 'Plablack 15157' | 11.4-12.3 | 9.6-10.0 |
| 'Reuben' (U.S. Plant Pat. No. 23,497) | 7.0-10.0 | 7.9-8.40 |
| 'Prim ARK-45' | 9.2-11.2 | 10.7-9.80 |

WEIGHT is shown as the average weight per fruit (g/fruit) in First Quality Fruits.

Table 6 shows a comparison of the fruit analysis between the new variety 'Plablack 115157' and its closest varieties 'Reuben' (U.S. Plant Pat. No. 23,497) and Prim ARK:45.

TABLE 6

FRUIT ANALYSIS

| | 'Reuben' (U.S. Plant Pat. No. 23,497) | 'Plablack 15157' 915.21R.06) | 'Prim ARK-45' |
|---|---|---|---|
| Firmness (Kg) | 0.20 | 0.60 | 0.30 |
| Humidity & Volatile Matter (%) | 84.60 | 81.90 | 84.30 |
| Dry Matter (%) | 15.40 | 18.10 | 15.70 |
| pH (to 20°) | 3.40 | 3.40 | 3.40 |
| Acidity as Anhydride Citric (%) | 0.70 | 0.80 | 0.76 |
| Soluble Solids (° Brix) | 10.60 | 12.40 | 13.60 |
| Maturity Index | 15.10 | 15.50 | 17.90 |
| Content in Ascorbic Acid (ppm) | 25.00 | 26.20 | 25.00 |

TABLE 6-continued

FRUIT ANALYSIS

| | 'Reuben' (U.S. Plant Pat. No. 23,497) | 'Plablack 15157' 915.21R.06) | 'Prim ARK-45' |
|---|---|---|---|
| Dominant Tonality (nm) | 345 | 325 | 320 |
| Luminosity: Transmittance to 460 nm | 41.5 | 49.4 | 46.0 |

The following definitions apply:

Firmness refers to the fruit's resistance to penetration measured in Kilograms (Kg). The measure given has been obtained by the penetrometer ROZE Mod. Arbelette, with a 50 $mm^2$ section head.

Dry Matter refers to the residual weight left from the trituration of the fruit after the drying process at a temperature of 103° C.±2° C. until reaching constant weight. (%) Dry Matter=(Weight Dry Matter/Weight Fresh Matter)×100

Humidity & Volatile Matter represents the content in volatile matters and water of the fruits. (%) Humidity & Volatile Matter=100: % Dry Matter Maturity Index refers to the relation between Soluble solids and Acidity as Anhydride Citric.

Maturity Index=Soluble solids/Acidity as Anhydride Citric

DETAILED DESCRIPTION OF THE NEW VARIETY

Variety: 'Plablack 15157'. Breeder Ref. 15.21R.06

Classification: *Rubus* subgenus *Eubatus* sect. *Morifieri* & *Ursini* and hybrids.

Plants are growing in containers of 50 liters of capacity and they are described during cultivar's primocane.

Plant:

*Habit*.—Upright.

*Vigor*.—Strong.

Dormant cane:

*Length*.—About 180 cm to 200 cm.

*Diameter*.—About 1.0 cm to 1.5 cm.

*Texture*.—Smooth.

*Internode length*.—About 6.0 to 8.0 cm.

*Pubescence*.—Few and downward.

*Anthocyanin coloration*.—Absent.

*Color*.—RHS Green group (near 143 C to 143 B).

Young shoot:

*Length*.—About 170 cm to 180 cm.

*Diameter*.—About 0.9 cm to 1.2 cm.

*Texture*.—Smooth.

*Internode length*.—About 4.0 cm to 5.0 cm.

*Pubescence*.—Few and downward.

*Anthocyanin coloration during rapid growth*.—Very spread (RHS Greyed-Orange group near 175 D to 176 D).

*Color*.—RHS Green group (near 143 C to 143 B).

Spines:

*Shape*.—Conical.

*Density*.—High.

*Number/cm*.—About 3 to 5 in dormant canes and about 4 to 6 in young shoots.

*Length*.—About 6.5 mm to 8.5 mm.

*Width*.—About 4.0 mm to 5.5 mm at the base.

*Apex*.—Straight.
*Texture*.—Rigid.
*Color at base in dormant cane*.—RHS Green group color (near 145 D to 145 C).
*Color at tip in dormant cane*.—RHS Greyed-Orange group color (near 176 C to 176 B).
*Color at base in young shoot*.—RHS Green group color (near 142 B to 142 A).
*Color at tip in young shoot*.—RHS Green group color (near 142 C to 142 B).
*Attitude of apex in relation to cane*.—Downwards.

Leaf:
*Type*.—Palmate.
*Number of leaflets*.—3 to 5.
*Arrangement of lateral leaflets*.—Free.
*Overlapping of lateral leaflets with terminal leaflet*.—Touching.
*Upperside*.—RHS Green group (near 141 C to 141 B).
*Underside*.—RHS Green group color (near 143 B to 143 A).
*Length*.—About 18.0 cm to 19.0 cm.
*Width*.—About 15.5 cm to 16.5 cm.
*Profile of leaflets in cross section*.—V-shaped.
*Relief between veins*.—Weak to medium.
*Upperside glossinesss*.—Strong.

Lateral leaflet:
*Shape*.—Elliptic.
*Length*.—About 9.0 cm to 9.5 cm.
*Width*.—About 5.5 cm to 6.0 cm.
*Shape of tip*.—Acuminate.
*Shape of base*.—Obtuse.
*Shape of margin*.—Bi-serrate.
*Upperside rugosity*.—Weak to medium.
*Underside texture*.—Medium.
*Upperside*.—RHS Green group (near 141 C to 141 B).
*Underside*.—RHS Green group color (near 143 B to 143 A).
*Venation pattern*.—Penniveined.
*Upperside venation coloration*.—RHS Yellow-Green group color (near 144 C to 144 B).
*Underside venation coloration*.—RHS Yellow-Green group color (near 144 C to 144 B).

Terminal leaflet:
*Length/width ratio*.—Longer than broader.
*Length*.—About 10 cm to 11.0 cm.
*Width*.—About 6.5 cm to 7.0 cm.
*Cross section*.—Concave.
*Upperside*.—RHS Green group (near 141 C to 141 B).
*Underside*.—RHS Green group color (near 143 B to 143 A).
*Shape of leaflet*.—Ovate.
*Shape of tip*.—Acuminate.
*Shape of base*.—Rounded.
*Shape of margin*.—Bi-serrate.
*Upperside rugosity*.—Weak to medium.
*Underside texture*.—Medium.
*Venation pattern*.—Penniveined.
*Upperside venation coloration*.—RHS Yellow-Green group color (near 144 C to 144 B).
*Underside venation coloration*.—RHS Yellow-Green group color (near 144 C to 144 B).

Rachis:
*Length between the terminal leaflet and adjacent lateral leaflet*.—About 2.5 to 3.0 cm.
*Coloration*.—RHS Yellow-Green group color (near 144 C to 144 B).

Petiole:
*Color*.—RHS Yellow-Green group color (near 144 C to 144 B).
*Length of petiole*.—About 5.0 to 5.5 cm.
*Length*.—About 2.0 to 2.5 mm. in the Petiole and about 1.5 to 2.0 mm. in the rachis.
*Spines*.—Very few.
*Petiole texture*.—Smooth.

Stipule:
*Quantity per leaf*.—2.
*Shape*.—Lanceolate and erect.
*Length*.—About 6.0 mm to 7.5 mm.
*Width*.—Narrow. About 0.7 mm to 0.8 mm.
*Color* (*both surfaces*).—RHS Green group color (near 143 C to 143 B).

Peduncle:
*Length*.—About 4.0 cm to 5.0 cm.
*Diameter*.—About 1.5 mm to 2.5 mm.
*Surface texture*.—Smooth.
*Density of spines*.—Medium.
*Color*.—RHS Yellow-Green group color (near 143 C to 143 B).

Flower bud:
*Shape*.—Rounded.
*Diameter*.—About 5.5 mm to 7.5 mm.
*Color*.—RHS Green group (near 139 C to 139 B).

Flower:
*Diameter*.—About 4.0 to 4.5 cm.
*Number of pistils per flower*.—About 115 to 125.
*Pistil length*.—About 3.7 to 4.1 mm.
*Ovary shape*.—Slightly reniform.
*Ovary length*.—About 1.2 mm to 1.6 mm.
*Ovary width*.—About 0.8 mm to 1.0 mm.
*Ovary color*.—RHS Green group color (near 142 D to 142 C).
*Style length*.—About 2.2 mm to 2.6 mm.
*Style color*.—RHS Green-White group color (near 157 D to 157 C).
*Number of stamens per flower*.—About 95 to 105.
*Stamen length*.—About 4.7 mm to 5.6 mm.
*Stamen shape*.—Cylindrical lengthened.
*Stamen color*.—RHS Yellow-Green group color (near 145 D).
*Pollen*.—Amount: Moderate to abundant.
*Pollen color*.—RHS Greyed-Orange group color (near 174 B to 174 A).

Petal:
*Number of petals per flower*.—About 5 to 6.
*Shape*.—Long flat elliptic shape.
*Length*.—About 1.9 cm to 2.2 cm.
*Width*.—About 1.1 cm to 1.3 cm.
*Apex shape*.—Rounded.
*Base shape*.—Narrow.
*Margin*.—Slightly uneven.
*Texture*.—Smooth.
*Color* (*both surfaces*).—RHS Red-Purple group (near 68 B to 68 A) and whitish pigmentation (RHS White group near 155 A) at the base.

Sepal:
*Number of sepals per flower*.—About 5 to 6.
*Shape*.—Triangular shape.
*Length*.—About 9.0 to 12.0 mm.
*Width*.—About 5.0 to 7.0 mm.

*Apex shape*.—Acuminate.
*Base shape*.—Large at the base forming the calyx.
*Margin*.—Smooth and regular.
*Texture*.—Smooth.
*Color*.—RHS Yellow-Green group near 143 C to 143 A).

Fruit:
*Shape*.—Elliptic to narrow oblate.
*Length*.—About 3.9 cm to 4.5 cm.
*Width*.—About 2.9 cm to 3.4 cm.
*Color*.—RHS Black group near 202 A.
*Number of drupelets per fruit*.—About 110 to 120.
*Size of single drupelet*.—About 3.0 mm to 4.50 mm.
*Drupelet arrangement around the berry*.—Slightly irregular.
*Glossiness*.—Strong.
*Firmness*.—Medium.

Seed:
*Number of seeds per drupelet*.—1.
*Shape*.—Slightly reniform.
*Color*.—RHS Greyed-Orange group (near 165 C to 165 B).
*Surface texture*.—Wrinkled.

Fruiting lateral cane:
*Number of fruit per fruiting lateral cane*.—About 15 to 25 fruits.
*Average number of fruit per node*.—About 1 to 3 fruit.

Fruit bearing type: Both on previous year's cane in autumm and current year's cane in spring. 'Plablack 15157' has not been grown in all environments including harsh winter and summer environments. Cold tolerance and heat tolerance are expected to be high.

General: The growing period in Huelva, Spain, where the observations on primocane production were made, is between about June 1 and July 1 of the following year. 'Plablack 15157' is a primocane variety, with consistent fruit production from beginning October through ending December on primocanes and in the ensuing year from beginning May through the middle of June. After planting as aforesaid, plants are grown in raised beds under tunnel. Water and fertilizer were applied through drip irrigation.

Each year:
*Planting date*.—About June 1 in Cartaya (Huelva), Spain, about 7°W, 37°N, 45 feet elevation.

Fall production in same year:
10% *flowering*.—About September 1.
*Time of flowers* (50% *of plants at first flower*).—About September 15.
*First mature fruits*.—About October 1.
*Maturity* (15:20 *g/plant*).—About October 31.

Spring production in the ensuing year:
10% *flowering*.—About April 5.
*Time of flowers* (50% *of plants at first flower*).—About April 15.
*First mature fruits*.—About April 28.
*Maturity* (15:20 *g/plant*).—About May 5.

Storage qualities: 'Plablack 15157' fruit maintains their quality characteristics when keeping them in a frigo chamber at temperatures of about 2° C. during 48 hours. The fruit's color remains substantially the same. Shelf life of 'Plablack 15157' is medium to high: 8 to 11 days at temperatures about 4 to 5° Centigrade.

Use/market: The berries of 'Plablack 15157' are suitable for consumption as fresh fruit. Also, they are amenable to processing.

Disease resistance: No particular sensitivity to any disease or pest has been observed for 'Plablack 15157'.

I claim:

1. A new and distinct blackberry plant of the variety substantially as shown and described.

* * * * *